United States Patent

Varma et al.

Patent Number: 4,695,585
Date of Patent: Sep. 22, 1987

[54] 7-OXABICYCLO(2.2.1)HEPTANE ANALOGS USEFUL AS INHIBITORS OF 5-LIPOXYGENASE AND CYCLOOXYGENASE

[75] Inventors: Ravi K. Varma, Belle Mead; Eric M. Gordon, Pennington, both of N.J.

[73] Assignee: E. R. Squibb & Sons, Inc., Princeton, N.J.

[21] Appl. No.: 910,583

[22] Filed: Sep. 23, 1986

[51] Int. Cl.$^4$ .................. A61K 31/34; C07D 307/00
[52] U.S. Cl. .................. 514/469; 549/463; 514/863; 514/826
[58] Field of Search .......... 549/463; 514/469, 826, 514/863

[56] References Cited

U.S. PATENT DOCUMENTS

| | | | |
|---|---|---|---|
| 4,143,054 | 3/1979 | Sprague | 549/463 |
| 4,254,044 | 3/1981 | Sprague | 549/463 |
| 4,536,513 | 8/1985 | Das et al. | 549/463 |
| 4,582,854 | 4/1986 | Hall et al. | 549/463 |

FOREIGN PATENT DOCUMENTS 0083204 12/1982 European Pat. Off. .

Primary Examiner—Henry R. Jiles
Assistant Examiner—Bernard I. Dentz
Attorney, Agent, or Firm—L. S. Levinson; T. R. Furman, Jr.

[57] ABSTRACT

A compound of the formula

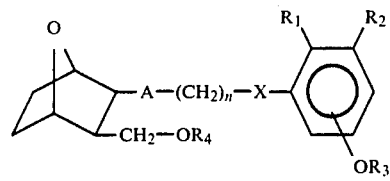

wherein $R_1$ is hydrogen, hydroxy, alkoxy or aryloxy; $R_2$ is hydrogen, hydroxy, alkoxy or aryloxy; or wherein $R_1$ and $R_2$ taken together is an aromatic ring; $R_3$ is hydrogen or lower alkyl; $R_4$ is lower alkyl, substituted alkyl, alkenyl or alkynyl; X is amino, alkylamino, alkanoylamino, oxygen or a single bond; A is $CH_2$—$CH$=$CH$ or a single bond; and n is an integer from 0 to 9, with the proviso that when A is a single bond, n is an integer from 1 to 9 including all stereoisomers thereof.

These new compounds have been found to simultaneously inhibit the arachidonic acid enzymes 5-lipoxygenase and cyclooxygenase and as such are useful, for example, as antiinflammatory agents.

28 Claims, No Drawings

7-OXABICYCLO(2.2.1)HEPTANE ANALOGS USEFUL AS INHIBITORS OF 5-LIPOXYGENASE AND CYCLOOXYGENASE

FIELD OF THE INVENTION

The present invention relates to 7-oxabicyclo(2.2.1-)heptane analogs and more particularly concerns such analogs which simultaneously inhibit the arachidonic acid enzymes 5-lipoxygenase and cyclooxygenase and as such are useful, for example, as antiinflammatory agents.

BACKGROUND OF THE INVENTION

In a copending application entitled "7-OXABICYCLO(2.2.1)HEPTANE HYDROXAMIC ACID DERIVATIVES USEFUL AS 'DUAL INHIBITORS'", Ser. No. 900,565 on Aug. 26, 1986, compounds are disclosed having the general formula

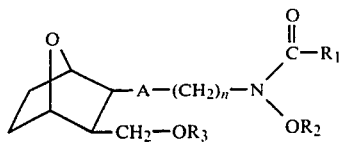

wherein $R_1$ is hydrogen, lower alkyl, aryl, aralkyl or alkenyl; $R_2$ is hydrogen, lower alkyl, alkanoyl or aroyl; $R_3$ is lower alkyl, alkenyl or alkynyl; A is —$CH_2$—CH=CH— or a single bond; and n is an integer from 0 to 9, with the proviso that when A is a single bond, n is an integer from 1 to 9; and including all stereoisomers and pharmaceutically acceptable salts thereof. These compounds are "dual inhibitors", i.e. they are capable of simultaneously inhibiting the arachidonic acid enzymes 5-lipoxygenase and cyclooxygenase, thereby preventing the formation of various leukotrienes and prostaglandins. As such, these compounds can be employed as, for example, antiinflammatory, antiallergy, antiasthma and antipsoriatic agents.

SUMMARY OF THE INVENTION

In accordance with the present invention new 7-oxabicyclo(2.2.1)heptane analogs, such as phenols, naphthols, alkoxy phenols, alkoxy naphthols, amino phenols, amino naphthols, amido phenols and amido naphthols, useful as inhibitors of the arachidonic acid enzymes 5-lipoxygenase and cyclooxygenase are provided. These new compounds have the general formula

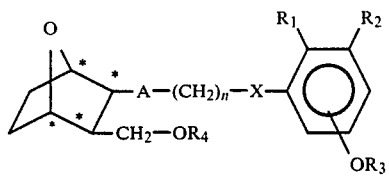

wherein $R_1$ is hydrogen, hydroxy, alkoxy or aryloxy; $R_2$ is hydrogen, hydroxy, alkoxy or aryloxy; or wherein $R_1$ and $R_2$ taken together is an aromatic ring; $R_3$ is hydrogen or lower alkyl; $R_4$ is lower alkyl, alkenyl or alkynyl; X is, amino, alkylamino, alkanoylamino, oxygen or a single bond; A is—$CH_2$—CH=CH or a single bond; and n is an integer from 0 to 9, with the proviso that when A is a single bond, n is an integer from 1 to 9; including all stereoisomers thereof.

DETAILED DESCRIPTION OF THE INVENTION

The term "lower alkyl" or "alkyl" as employed herein by itself or as part of another group includes both straight and branched chain radicals of up to 12 carbons, preferably 1 to 8 carbons, such a methyl, ethyl propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an aralkyl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkylthio substituent.

The term "alkylamino" employed herein by itself or as part of another group includes methylamino, dimethylamino and the like.

The term "alkanoylamino" employed herein by itself or as part of another group includes acetylamino, acetylmethylamino and the like.

The term "cycloalkyl" employed herein by itself or as part of another group includes saturated cyclic hydrocarbon groups containing 3 to 12 carbons preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or aryl-lower alkyl" as used herein refers to lower alkyl groups as discussed above having an aryl substituent, such as benzyl.

The term "lower alkenyl" or alkenyl" as employed herein by itself or as part of another group includes an unsaturated hydrocarbon group having from 2 to 8 carbons and a single carbon-carbon double bond, such as ethenyl, 1-propenyl, 2-propenyl, 1-butenyl, 2-butenyl, 3-butenyl and the like.

The term "lower alkynyl" or alkynyl" as employed herein by itself or as part of another group includes an unsaturated hydrocarbon group having from 2 to 8 carbons and a single carbon-carbon triple bond, such as ethynyl, 1-propynyl, 2-propynyl, 1-butynyl, 2-butenyl, 3-butenyl and the like.

The term "halogen" or halo" as used herein refers to chlorine, bromine, fluorine or iodine with chlorine being preferred.

Preferred are those compounds of the invention wherein $R_1$ is OH, $R_2$ is $NH_2$ or OH, $R_3$ is H, $R_4$ is n-hexyl, A is $CH_2$—CH=CH, X is O or $CH_2$, and n=3.

The various compounds of the invention may be prepared as described below.

To make phenol or naphthol derivatives of the invention, that is, compounds of formula I wherein X is a single bond and $R_1=R_2=H$, a compound of the formula

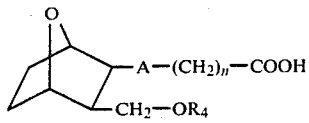
II (the preparation of which is described in U.S. Pat. No. 4,582,854) can be reacted with a reducing agent, e.g. lithium aluminum hydride, in the presence of a dry organic solvent, e.g. tetrahydrofuran, to provide the alcohol

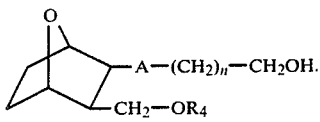
III

Compound III can thereafter be reacted with triphenylphosphine and N-bromosuccinimide in the presence of a solvent, e.g. benzene, and methylenechloride to produce the bromide

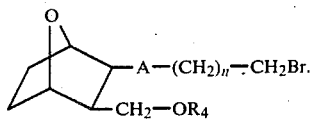
IV (wherein n is the integer of the desired final product) can be refluxed under nitrogen in the presence of triphenyl phosphine and an organic solvent, such as acetonitrile to afford

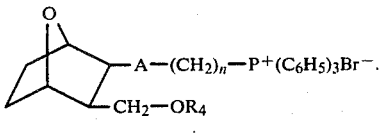
V

Compound V, in a dry organic solvent, e.g. tetrahydrofuran, and in the presence of potassium-t-amylate in toluene, can thereafter be reacted with a compound of the formula

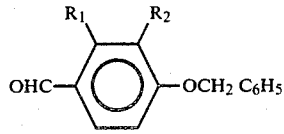
VI which compound (VI) is formed by the reaction of a hydroxybenzaldehyde wherein $R_1$ and $R_2$ are hydrogen, benzyloxy, alkoxy or aryloxy or $R_1$ and $R_2$ taken together is an aromatic ring, in the presence of dimethylformamide and a base, e.g. potassium carbonate, with benzyl bromide. The above reaction of compounds V and VI provides a compound having the formula

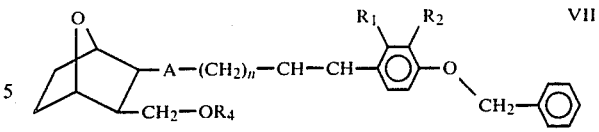
VII

Compound VII in the presence of a solvent, e.g. methanol, can be reacted with hydrogen gas in the presence of a catalyst like palladium on carbon to provide compounds of the invention

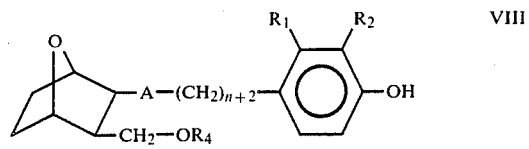
VIII that is, compounds of formula I wherein X is a single bond and wherein $R_1$ and $R_2$ can be hydrogen, hydroxy, alkoxy or aryloxy in the case of phenols and further wherein $R_1$ and $R_2$ taken together is an aromatic ring in the case of naphthols.

To make alkoxy phenol and alkoxy naphthol derivatives of formula I, that is, compounds wherein X is oxygen, compound III, in the presence of tetrahydrofuran and diethyl azodicarboxylate, can be reacted with a compound of the formula

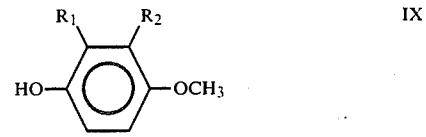
IX and triphenylphosphine at a temperature in the range of from about 0° C. to about 60° C. to afford the compounds of the invention

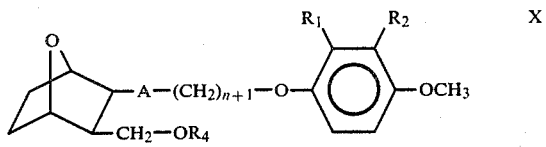
X wherein $R_1$ and $R_2$ are independently the aforementioned substituents of the invention when compound X is a phenol derivative or wherein $R_1$ and $R_2$ taken together is an aromatic ring when compound X is a naphthol derivative.

While compound X represents the alkoxy phenol- and alkoxy naphthol- derivatives of formula I wherein $R_3$ is methyl, the compound of formula X in the presence of dimethylformamide can be reacted with an N-alkylthiol to provide

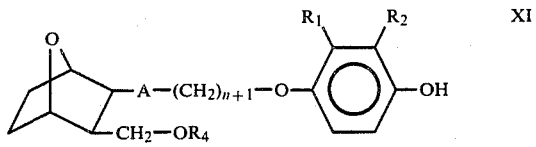
XI that is, the alkoxy phenol or alkoxy naphthol-derivatives of formula I wherein $R_3$ is hydrogen. While compound XI represents a benzyloxy phenol, i.e. compounds where $R_1$ and $R_2$ are benzyloxy, compound XI is further reacted with hydrogen in the presence of a catalyst such as palladium on carbon in the presence of a solvent, e.g. methanol, to provide comounds of the formula I where $R_1$ and $R_2$ are OH. Alternatively, the bromide IV can thereafter be reacted with compound IX in the presence of a base, e.g. potassium carbonate, and a solvent, e.g. dimethylformamide to provide the compounds of formula X.

To make the amino phenol- and amino naphthol derivatives of the invention, that is, compounds of formula I wherein X is amino or alkylamino, the bromide IV can be reacted with a compound of the formula

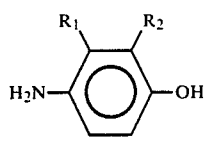
XII in the presence of a mild base, e.g. sodium bicarbonate and a solvent, e.g. hexamethylphosphoric triamide or N,N-dimethylformamide to provide

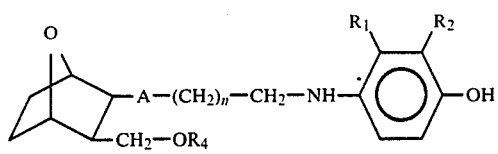
XIII that is, compounds of the invention wherein x is alkylamino.

To make the amidophenol-and amidonaphthol-derivatives of the invention, that is, compounds of formula I wherein X is alkanoylamino, the carboxylic acid of formula II is reacted with a chlorinating agent, e.g. oxalyl chloride, in the presence of an organic solvent, e.g benzene, to provide a compound of the formula

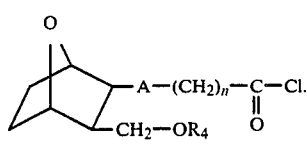
XIV

Compound XIV can thereafter be reacted with compound XII in the presence of a base to provide

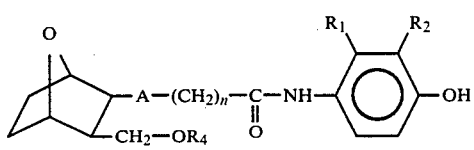
XV that is, compounds of formula I wherein X is alkanoylamino.

The compounds of this invention have four centers of asymmetry as indicated by the asterisks in formula I. However, it will be apparent that each of the formulae set out above which do not include asterisks still represent all the possible stereoisomers thereof. All of the various stereoisomeric forms are within the scope of the present invention.

The various stereoisomeric forms of the compounds of the invention, namely, cis-endo, cis-exo and trans forms and their optical isomers may be prepared as shown in the working Examples which follow and by employing starting materials and following the procedures as outlined in U.S. Pat. No. 4,582,854. Examples of such stereoisomers are set out below.

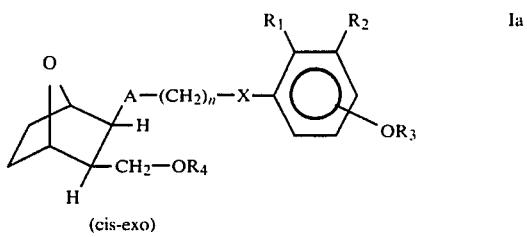
Ia
(cis-exo)

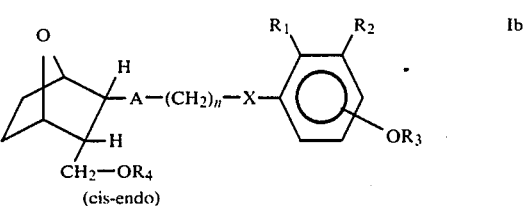
Ib
(cis-endo)

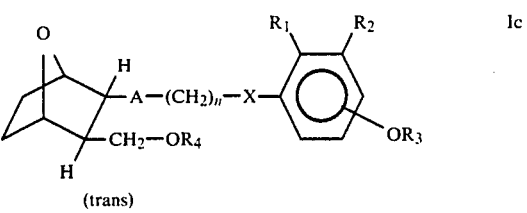
Ic
(trans)

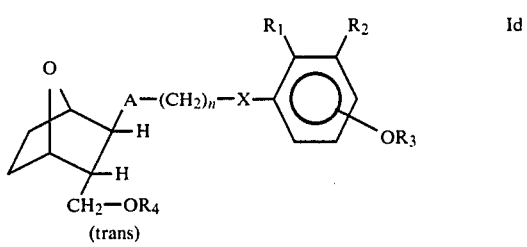
Id
(trans)

The nucleus in each of the compounds of the invention is depicted as

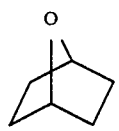

for matter of convenience; it will also be appreciated that the nucleus in the compounds of the invention may be depicted as

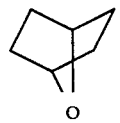

The compounds of the invention are inhibitors of the arachidonic acid enzymes 5-lipoxygenase and cyclooxygenase and prevent formation of certain leukotriene and prostaglandins. The administration of compounds of this invention to humans or animals provides a method for treating allergy of a reagin or non-reagin nature. Asthma and psoriasis are preferably treated but any allergy or inflammation wherein leukotrienes or prostaglandins are thought to be involved as pharmacological mediators can be treated. For example, the compounds of this invention can be used for treatment of such conditions as allergic rhinitis, food allergy and urticaria, as well as asthma and psoriasis.

An effective but essentially non-toxic quantity of the compound is employed in treatment.

The compounds of the invention can be administered orally, parenterally or topically to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, cream, ointment or suspension containing about 5 to about 5000 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention.

EXAMPLE 1

[1R-[[1α,2β,3β,4α]]-4-[7-[3-[(Hexyloxy)methyl]-7-oxabicyclo[2.2.1]hept-2-yl]heptyl]phenol

A.

[1R-[1α,2β(Z),3β,4α]-6-[3-[(Hexyloxy)methyl]-7-oxabicyclo[2.2.1]hept-2-yl]-4-hexenoic acid methyl ester A solution of [1R-[α,2β(Z),3β,4α]-6-[3-[(Hexyloxy)methyl]-7-oxabicyclo[2.2.1]-hept-2-yl]-5-hexenoic acid (900 mg, 2.66 mmole) in dry ether (50 ml) was treated with an excess of diazomethane in ether and stirred at room temperature for one hour. The excess diazomethane was blown off with a stream of nitrogen and the colorless solution evaporated to dryness. The residual oil was chromatographed to give 1.1 g of title A compound as an oil.

B.

1R-[1α,2β(Z),3β,4α]-6-[3-[(Hexyloxy)methyl]-7-oxabicyclo[2.2.1hept-2-yl]-4-hexenol A solution of title A compound (2.1 g, 6.55 mmole) in dry tetrahydrofuran (10 ml) was added dropwise to a suspension of lithium aluminum hydride (410 mg, 10.8 mmole) in dry tetrahydrofuran (50 ml) under nitrogen at ~0° C. The mixture was stirred at 0° C. for 30 minutes and at room temperature for 2.5 hours, then quenched by the addition of water (0.41 ml), diluted with ether (200 ml) and filtered, washing the precipitates well with ether (50 ml). The filtrate was dried over anhydrous magnesium sulfate, filtered and evaporated to dryness to give 1.93 g of title B compound as a homogeneous oil.

C.

1R-[1α,2β(Z),3β,4α]-6-[3-[(Hexyloxy)methyl]-7-oxabicyclo[2.2.1]hept-2-yl]-bromo-4-hexene A mixture of triphenylphosphine (901 mg, 3.4 mmole), N-bromosuccinimide (611.7 g) and dry Celite (2.0 g) in a mixture of benzene (20 ml) and dry dichloromethane (5 ml) was stirred at 0° C. under nitrogen for 10 minutes and at room temperature for one hour. A solution of title B compound (500 mg, 1.71 mmole) in dry dichloromethane (5 ml) was added to the complex and stirring continued at room temperature for 20 hours. The mixture was diluted with dichloromethane, stirred and filtered, washing the solids with more dichloromethane (50 ml). The organic extracts were evaporated to dryness and the residual oil partitioned twice between water (25 ml) and dichloromethane (25 ml). The organic phase was dried over anhydrous magnesium sulfate, filtered and evaporated to dryness to give an oil containing traces of starting material and triphenylphosphine. The crude product was chromatographed on a silica gel column to give 519 mg of title C compound as a homogeneous oil.

D.

1R-[1α,2β(Z),3β,4α]-6-[[3-[(Hexyloxy)methyl]-7-oxabicyclo[2.2.1]hept-2-yl]-4-hexenyl]-triphenyl phosphonium bromide A solution of title C compound (373 mg, 1 mmole) and triphenylphosphine (262 mg, 1 mmole) in dry acetonitrile (10 ml) was refluxed under an atmosphere of nitrogen for 72 hours. Most of the acetonitrile was then evaporated in vacuo and the residual gum was washed three times with ether. The gummy residue was dried in vacuo at -60° to afford 602 mg of the title D compound.

E. p-Benzyloxy-benzaldehyde

A solution of p-hydroxybenzaldehyde (3.66 g, 30 mmole) in dry DMF (20 ml) was stirred with anhydrous potassium carbonate (12.5 g, 90 mmole) and benzylbromide (6.16 g, 36 mmole) was added. After 18 hours, the mixture was diluted with brine (75 ml) and extracted three times with ether. The extracts were combined, washed with dilute brine, dried over anhydrous magnesium sulfate and evaporated in vacuo to afford a solid. Crystallization from ethyl ether in hexane gave 5 g of title E compound as light yellow flakes, with consistent spectral data.

F.

1-R[1α,2β(1EZ,5Z),3β,4α]-7-[4-[[3-(Hexyloxy)-methyl]-7-oxabicyclo[2.2.1]hept-2-yl]-benzyloxyphenyl]-hepta-1,5-diene A solution of title D compound (602 mg, 0.95 mmole) in dry THF (20 ml) was cooled and stirred in an ice bath under nitrogen and a 1.7M solution of potassium-t-amylate in toluene (0.55 ml, 0.94 mmole) was added. A red solution was produced. After ten minutes a solution of title E compound (212 mg, 1 mmole) in dry THF (5 ml) was added. After 30 minutes, the mixture was diluted with water (10 ml), concentrated in vacuo, diluted with brine (50 ml) and extracted three times with ether. The extracts were combined, washed with dilute brine, dried over anhydrous magnesium sulfate and evaporated to afford the crude product as an oil. This was chromatographed on a column of silica gel to give 380 mg of the title F compound, with consistent spectral data.

G.
[1R-[[1α,2β,3β,4α]]-4-[7-[3-[(Hexyloxy)-methyl]-7-oxabicyclo2.2.1]hept-2-yl]heptyl]-phenol A solution of title F compound (380 mg, 0.774 mmole) in methanol (30 ml) was stirred with 10% palladium on carbon (50 mg) under an atmosphere of hydrogen for 3 hours. It was then filtered through a bed of Celite and evaporated to afford the product as an oil. It was chromatographed on a column of silica gel to give 290 mg of the title compound, with consistent spectral data.

EXAMPLE 2

[1R-[1α,2β(Z),3β,4α]]-3-[(Hexyloxy)methyl]-2-[5-(3,4,5-trimethoxyphenoxy)-2-pentenyl-7-oxabicyclo[2.2.1]heptane

A. 1-Iodo-3[(tetrahydro-2-pyranyl)oxy]-propane

A solution of 3-iodopropanol (15 g, 80.65 mole), dihydropyran (14.7 ml, 161.29 mole) and pyridium p-toluenesulfonate (500 g, 2.0 mole) in 100 ml of dry dichloromethane was stirred at room temperature under an atmosphere of nitrogen for 2.5 hours. The resulting mixture was diluted with dichloromethane (150 ml), washed with water and a saturated sodium bicarbonate solution, dried over anhydrous magnesium sulfate and evaporated in vacuo. The residue was flash chromatographed on a silica gel to give 20.43 g of title A compound as an oil, with consistent spectral data.

B. 1[3[(Tetrahydro-2-pyranyl)oxy]-propyl]-triphenyl phosphonium iodide

A solution of title A compound (20.43 g, 75.63 mmole) and triphenylphosphine (19.84 g, 75.63 mmole) in 150 ml of dry benzene was refluxed under an atmosphere of nitrogen for 24 hours. The solvent was evaporated in vacuo to give a sticky gum. This was rinsed with acetonitrile (80 ml) when a white solid precipitated out. The solid was filtered and dried over phosphorus pentoxide at 60° C. in vacuo for 20 hours to give 32.8 g of title B compound, with consistent spectral data.

C.
1R-[1α,2β(Z),3β,4α]-[[1[5-[3(Hydroxy)-methyl]-7-oxabicyclo[2.2.1]hept-2-yl]-tetrahydro-2-pyranyl]oxy]-3-pentene To a chilled and stirred slurry of title B compound (4.224 g, 9 mmole) in 40 ml of dry tetrahydrofuran was added dropwise potassium-t-amylate (4.03 ml, 1.74M in toluene) over five minutes under an atmosphere of nitrogen. The orange solution was stirred at −20° for 2 hours and then a solution of compound [4aR-(4aα,5α,-8α,8aα)]octahydro-5,8-epoxy-(1H)-benzopyran-3-ol (510 mg, 3 mmole) in 10 ml of dry tetrahydrofuran was added dropwise. The solution was gradually warmed up to room temperature, stirred for 18 hours and quenched with acetaldehyde (1.5 ml). After stirring at room temperature for another 30 minutes, the mixture was diluted with 30 ml of a saturated sodium bicarbonate solution and extracted three times with ethyl ether. The combined ether extracts were washed with brine, dried over anhydrous magnesium sulfate and evaporated in vacuo. The residue was flash-chromatographed on a silica gel to give 810 g of title C compound as an oil, with consistent spectral data.

D.
1-R[1α,2β(Z),3β,4α]-[[1[5-[3-(Hexyloxy)-methyl]-7-oxabicyclo[2.2.1]hept-2-yl]-tetrahydro-2-pyranyl]oxy]-3-pentene Powdered potassium hydroxide (900 mg, 16 mmole) in 80 ml of dry xylene was refluxed under stirring in an atmosphere of nitrogen and 35–40 ml of xylene was removed by distillation. To this was added dropwise a solution of title C compound (400 mg, 1.35 mmole) and n-hexylmesylate (1.216 g, 6.75 mmole) in 25 ml of dry xylene. The mixture was refluxed for one hour and was then cooled. Water (25 ml) was added and the solution was extracted three times with ethyl ether. The combined ether extracts were washed with brine, dried over anhydrous magnesium sulfate and evaporated in vacuo. The residue was flash chromatographed on a silica gel to give 455 mg of title D compound as an oil, with consistent spectral data.

E.
1R-[1α,2β(Z),3β,4α]-1-[5[3(Hexyloxy)methyl]-7-oxabicyclo[2.2.1]hept-2-yl]pentene-3-ol A solution of title D compound (125 mg, 0.328 mmole) and pyridium p-toluenesulfonate (91 mg, 0.361 mmole) in 5 ml of methanol was stirred at 70° under an atmosphere of nitrogen for 1.5 hours. The methanol was mostly removed in vacuo, the residue diluted with 15 ml of water and extracted three times with ethyl ether. The combined ether extracts were washed with brine, dried over anhydrous magnesium sulfate and evaporated in vacuo. The residue was flash chromatographed on a silica gel to give 85 mg of title E compound.

F.
[1R-[1α,2β(Z),3β,4α]]-3-[(Hexyloxy)methyl]-2[5-(3,4,5-trimethoxyphenoxy)-2-pentenyl]-7-oxabicyclo[2.2.1]heptane To a chilled and stirred solution of title E compound (147.2 mg, 0.5 mmole), triphenylphosphine (164 mg, 0.625 mmole) and 3,4,5-trimethoxyphenol (115 mg, 0.625 mmole) in dry tetrahydrofuran (3 ml) under an atmosphere of nitrogen was added dropwise diethyl azodicarboxylate (99 μl, 0.625 mmole) over five minutes. After 30 minutes at 0°, the reaction was allowed to warm to room temperature for 3.5 hours. The solvent was evaporated by a stream of nitrogen. The residue was flash chromatographed on a column of silica gel to give 115 mg of the title compound, with consistent spectral data.

EXAMPLE 3

[1R-[1α,2β(Z),3β,4α]]-5-[[5-[3-[(Hexyloxy)-methyl]-7-oxabicyclo[2.2.1]hept-2-yl]-3-pentenyl]oxy]-2,3-dimethoxyphenol To a stirred suspension of 50% sodium hydride-paraffin (155 mg, 3.23 mmole) in dry dimethylformamide (4 ml) under an atmosphere of nitrogen was carefully added n-propanethiol (0.325 ml, 3.59 mmole). After 30 minutes, a solution of the title compound from Example 2 (200 mg, 0.434 mmole) was added and the mixture was heated at 100° for 24 hours. The mixture was then cooled to room temperature, acidified with 5% hydrochloric acid, diluted with brine (25 ml) and extracted three times with ethyl ether. The combined ether extracts were dried over anhydrous magnesium sulfate and evaporated in vacuo to give an oil. This was flash chromatographed on a column of silica gel to give 110 mg of the title compound as an oil, with consistent spectral data.

EXAMPLE 4

[1R-[1α,2β,3β,4α]]-4-[[7-[3-(Hexyloxy)-methyl]-7-oxabicyclo[2.2.1]hept-2-yl]-heptyl]oxy]-1,2-benzenediol

A.

[1R-[1α,2β(Z),3β,4α]]-4-[[7-[3-(Hexyloxy)-methyl]-7-oxabicyclo[2.2.1]hept-2-yl]-heptyl]oxy]-1,2-dibenzyloxy benzene A mixture of 1R-[1α,2β(Z),3β,4α]-7-[3[(Hexyloxy)-methyl]-7-oxabicyclo[2.2.1]hept-2yl]bromo-5-heptene (400 mg, 1.03 mmole; prepared using the procedure of Example 1, step C), 3,4-dibenzyloxyphenol (355.4 mg, 1.16 mmole), anhydrous potassium carbonate (344 mg, 2.49 mmole) and sodium iodide (33 mg) in dry dimethylformamide (11.0 ml) was stirred at room temperature under nitrogen for 48 hours. The mixture was diluted with brine (55 ml) and extracted three times with ether. The combined organic extracts were washed with water (25 ml) and brine (25 ml), dried over anhydrous magnesium sulfate, filtered and evaporated to dryness to give an oil which contained the desired product as the major component, some starting material and traces of two more polar components. This mixture was chromatographed on a silica gel to give 376.2 mg of the title A compound as a homogeneous oil, with consistent spectral data.

B.

[1R-[1α,2β,3β,4α]]-4-[[7-[3-[(Hexyloxy)-methyl]-7-oxabicyclo[2.2.1]hept-2-yl]-heptyl]oxy]-1,2-benzenediol A solution of title A compound (376.2 mg, 0.61 mmole) in dry methanol (100 ml) containing 5% palladium on carbon was hydrogenated at room temperature for five hours. The suspension was filtered through a millipore unit and the clear filtrate evaporated to give an oil which contained the title compound and a less polar component. This mixture was chromatographed on a silica gel column to give the desired compound (102 mg) and the second component (158.7 mg) which by spectral data was shown to be the side-chain saturated monobenzyloxy derivative. Rehydrogenation of this component in dry methanol (50 ml) in the presence of 10% palladium on carbon gave, after column chromatography, an additional 73.4 mg of the title compound as an oil, with consistent spectral data.

EXAMPLE 5

[1R-[1α,2β(Z),3β,4α]]-3-[(Hexyloxy)methyl]-2-[7-(3,4-dimethoxyphenoxy)-2-heptenyl]-7-oxabicyclo[2.2.1]heptane A mixture of [1R[1α,2β(Z),3β,4α]]-7-[3[(Hexyloxy)-methyl]-7-oxabicyclo[2.2.1]hept-2-yl]-bromo-5-heptene (400 mg, 1.03 mmole; prepared using the procedure of Example 1, step C), 3,4-dimethoxyphenol (178.8 mg, 1.16 mmole), anhydrous potassium carbonate (344 mg, 2.49 mmole) and sodium iodide (33 mg) in dry dimethylformamide (11 ml) was stirred at room temperature under argon for 2.5 days. The mixture was diluted with brine (55 ml) and extracted three times with ether. The combined ethereal extracts were washed with water (25 ml), brine (25 ml), dried over anhydrous magnesium sulfate, filtered and evaporated to dryness to give an oil which contained the desired product as the major component, some starting material and traces of three other less polar components. This mixture was chromatographed on a silica gel column to give 315.6 g of the title compound as a homogeneous oil with consistent spectral data.

EXAMPLE 6

[1R-[1α,2β(Z),3β,4α]]-4-[5-[3-[(Hexyloxy)-methyl]-7-oxabicyclo[2.2.1]hept-2-yl]-3-pentenyl]oxy]-1-naphthalenol

A.

[1R-[1α,2β(Z),3β,4α]]-4-[[5-[3-[(Hexyloxy)-methyl]-7-oxabicyclo[2.2.1]hept-2-yl]-3-pentenyl]oxy]-1-methoxynaphthalene To a chilled and stirred solution of the title E compound of Example 2 (250 mg, 0.85 mmole), triphenylphosphine (278 mg, 1.06 mmole) and 4-methoxy-1-naphthol (184 mg, 1.06 mmole) in dry tetrahydrofuran (4 ml) under an atmosphere of nitrogen was added dropwise diethyl azodicarboxylate (167 μl, 1.06 mmole) over five minutes. After 30 minutes at 0°, the reaction was allowed to warm to room temperature for three hours. Chromatography of an aliquot indicated that there was about 25% unreacted compound. More triphenylphosphine (93 mg), 4-methoxyl-1-naphthol (62 mg) and diethyl azodicarboxylate (56 μl) were successively added and stirred for another two hours. The solvent was evaporated by a stream of nitrogen. The residue was dried in vacuo at room temperature for one hour and flash chromatographed on a column of silica gel to give 170 mg of title A compound as an oil, with consistent spectral data.

B.

[1R-[1α,2β(Z),3β,4α]]-4-[[5-[3-[(Hexyloxy)-methyl]-7-oxabicyclo[2.2.1]hept-2-yl]-3-pentenyl]oxy]-1-naphthalenol To a stirred suspension of 50% sodium hydride-paraffin (112 mg, 2.34 mmole) in dry dimethylformamide (5 ml) under an atmosphere of nitrogen was carefully added n-propanethiol (0.23 ml, 2.54 mmole). After 30 minutes, a solution of title A compound (265 mg, 0.585 mmole) in 2 ml of dry dimethylformamide was added and the mixture was heated to 100° for 24 hours. The mixture was then cooled to room temperature, acidified with 5% hydrochloric acid, diluted with brine (30 ml) and extracted four times with ethyl ether. The combined ether extracts were dried over anhydrous magnesium sulfate and evaporated in vacuo to give an oil. This was flash chromatographed on a column of silica gel to give 225 mg of the title compound as an oil, with consistent spectral data.

EXAMPLE 7

[1R-[1α,2β(5Z),3β,4α]]-4-[[7-[3-[(Hexyloxy)-methyl]-7-oxabicyclo[2.2.1]hept-2-yl]-5-heptenyl]oxy]-1-naphthalenol

A.

[1R-[1α,2β(5Z),3β,4α]]-7-[3-[(Hexyloxy)-methyl]-7-oxabicyclo[2.2.1]hept-2-yl]-bromo-5-heptene To a stirred mixture of dried Celite (7 g) and triphenylphosphine (524 mg, 2 mmole) in dry methylene chloride under an atmosphere of nitrogen was added N-bromosuccinimide (356 mg, 2 mmole). After the mixture was stirred for one hour, a solution of [1R-[1α,2β(Z),3β,4α]]-7-[3-[(Hexyloxy)-methyl]-7-oxabicyclo[2.2.1]hept-2-yl]-5-heptenol (324.5 mg, 1 mmole;

prepared using the procedure of Example 1, step B) was added. After four hours, the mixture was filtered and the solids were washed with small amounts of methylene chloride. The filtrate and washings were combined, evaporated in vacuo and the residual gum was purified by chromatography on silica gel to isolate 370 mg of the title A compound as an oil, with consistent spectral data.

B.
[1R-[1α,2β(5Z),3β,4α]]-4-[[7-[3-[(Hexyloxy)-methyl]-7-oxabicyclo[2.2.1]hept-2-yl]-5-heptenyloxy-1-methoxy naphthalene A solution of title A compound (360 mg, 0.93 mmole) and 4-methoxy-1-naphthol (195.1 mg, 1.12 mmole) in dry DMF (10 ml) containing potassium carbonate (311 mg, 2.25 mmole) and sodium iodide (30 mg) was stirred at room temperature under nitrogen for 24 hours. Then, dilute brine (50 ml) was added and the mixture was extracted three times with ethyl ether. The extracts were combined, washed twice with water, dried over anhydrous magnesium sulfate and evaporated to give a bluish-brown oil. This was chromatographed on a column of silica gel to isolate 442 mg of the title B compound as an oil, with consistent spectral data.

C.
[1R-[1α,2β(5Z)3β,4α]]-4-[[7-[3-[(Hexyloxy)-methyl]-7-oxabiyclo[2.2.1]hept-2-yl]-5-heptenyl]oxy-1-naphthalenol A suspension of 50% sodium hydride-paraffin (68 mg, 1.4 mmole) in dry DMF (5 ml) was stirred under nitrogen and n-propanethiol (114 mg, 1.5 mmole) was carefully added. After 30 minutes, a solution of the title B compound (220 mg, 0.46 mmole) in dry DMF (2 ml) was added and the mixture was heated in a bath at 110° C.-115° C. for 20 hours. It was then cooled to ambient temperature, diluted with 10% hydrochloric acid (5 ml) and brine (30 ml) and extracted three times with ether. The extracts were combined, washed with brine, dried over anhydrous magnesium sulfate, evaporated and the residual oil was chromatographed on a column of silica gel to isolate 190 mg of the title compound as a thick oil, with consistent spectral data.

EXAMPLE 8
[1R-[[1α,2β,3β,4α]]-4-[[5-[3-[(Hexyloxy)-methyl]-7-oxabicyclo[2.2.1]hept-2-yl]pentyl]oxy]-1-2-benzenediol

A.
1R-[[1α,2α,3β,4α]]-4-[[5-3-[(Hexyloxy)-methyl]-7-oxabicyclo[2.2.1]hept-2-yl]-pentyl]oxy]-1,2-dibenzyloxy-benzene To a chilled and stirred solution of the title E compound from Example 2 (294.22 mg, 1 mmole), triphenylphosphine (328 mg, 1.25 mmole) and 3,4-dibenzyloxyphenol (383 mg, 1.25 mmole) in dry tetrahydrofuran (10 ml) under an atmosphere of nitrogen was added dropwise diethyl azodicarboxylate (197 μl, 1.25 mmole) over five minutes. After 30 minutes at 0°, the reaction was allowed to warm to room temperature for another three hours. The solvent was evaporated in vacuo. The residue was flash chromatographed on a column of silica gel to give 480 mg of the title A compound as a solid, with consistent spectral data.

B.
[1R-[[1α,2β,3β,4α]]-4-[[5-[3-[(Hexyloxy)-methyl]-7-oxabicyclo[2.2.1]hept-2-yl]pentyl]-oxy]-1,2-benzenediol A solution of title A compound (480 mg, 0.82 mmole) containing a suspension of 10% palladium on carbon (45 mg) in 100 ml of methanol was hydrogenated under atmospheric pressure at room temperature for three hours and the mixture filtered through a bed of Celite to remove the catalyst. The filtrate was evaporated in vacuo. The residue was chromatographed on a column of silica gel to give 200 mg of the title compound as an oil, with consistent spectral data.

EXAMPLE 9
[1R-[1α,2β(5Z),3β,4α]]-4-[[7-[(Hexyloxy)methyl]-7-oxabicyclo[2.2.1]hept-2-yl]-5-heptenyl]-amino]phenol monohydrochloride A mixture of the title A compound of Example 7 (203 mg, 0.52 mmole), 98% 4-aminophenol (231.6 mg, 2.08 mmole, 4 eq.) and sodium bicarbonate (436.8 mg, 10 eq.) was heated in hexamethylphosphoric triamide (2.5 ml) under nitrogen at 55° C.-60° C. for two hours. The reaction mixture was cooled, diluted with water (10 ml) and extracted twice with ether (25 ml). The ethereal extracts were washed three times with water (15 ml), brine (15 ml), dried over anhydrous magnesium sulfate and evaporated to dryness. The residual violet-brown semi-solid (345 mg) was chromatographed on a silica gel column to give the free base of the title compound (200 mg). The free base was dissolved in ether (25 ml), 1.47M hydrochloric acid in methanol (0.35 ml) was added and evaporated to dryness to give 220 mg of the desired compound as a dark reddish-brown oil, with consistent spectral data.

EXAMPLE 10
[1R-[1α,2β(5Z),3β,4α]]-7-[3-[(Hexyloxy)methyl]-7-oxabicyclo[2.2.1]hept-2-yl]-N-(4-hydroxyphenyl)-2,2-dimethyl-5-heptenamide

A.
[1R[1α,2β(5Z),3β,4α]]-7-[3-[(Hexyloxy)-methyl]-7-oxabicyclo[2.2.1]hept-2-yl]-2-methyl-5-heptenoic acid, methyl ester A solution of diisopropylamine (404 mg, 4 mmole) in dry THF (75 ml) was cooled and stirred in a bath at −78° C. under nitrogen and 1.7M butyllithium in hexane (1.8 ml, 3 mmole) was added. After 5 minutes, a solution of [1R-[1α,2β(5Z),3β,-4α]]-7-[3-[(Hexyloxy)-methyl]-7-oxabicyclo[2.2.1]-hept-2-yl]-5-heptenoic acid, methyl ester (1.05 g, 3 mmole; the preparation of which is described in U.S. Pat. No. 4,582,854) in dry THF 12 ml was added dropwise in the course of 5 minutes. After another 15 minutes, methyl iodide (1.8 g, 12 mmole) was added. After 1.5 hours the solution was allowed to warm to room temperature in the course of about 30 minutes. The mixture was then poured into saturated brine (150 ml) and was extracted three times with ether. The extracts were combined, washed with water, dried over anhydrous magnesium sulfate and was evaporated to afford 1 g of the crude product as an oil. This was subjected to a flash chromatography on a silica gel column to isolate 650 mg of title A compound, with consistent spectral data.

B.
[1R[1α,2β(5Z),3β,4α]]-7-[3-[(Hexyloxy)-methyl]-7-oxabicyclo[2.2.1]hept-2-yl]-2,2-dimethyl-5-heptenoic acid, methyl ester A solution of dry isopropylamine (202 mg, 2 mmole) in dry THF (12 ml) was cooled and stirred in a bath at −78° under an atmosphere of nitrogen and 1.7M n-butyllithium in hexane (1.06 ml, 1.8 mmole) was added. After 5 minutes, a solution of title A compound (650 mg, 1.77 mmole) in dry THF (6 ml) was added in the course of 5 minutes. After 10 minutes, methyl iodide (850 mg, 6 mmole) was added. After 1.5 hours, the solution was warmed to room temperature in the course of about 30 minutes. It was then added into 2% hydrochloric acid (75 ml) and was extracted three times with ether. The extracts were combined, washed twice with water, dried over anhydrous magnesium sulfate and was evaporated to afford 640 mg of impure title C compound and an oil. This was subjected to a flash chromatography on silica gel to isolate 400 mg of title C compound, with consistent spectral data.

C.
[1R[1α,2β(5Z),3β,4α]]-7-[3-[(Hexyloxy)-methyl]-7-oxabicyclo[2.2.1]hept-2-yl]-2,2-dimethyl-5-heptenoic acid A solution of title B compound (233 mg, 0.61 mmole) in dioxane (3 ml) was mixed with 3N lithium hydroxide (1 ml) and was stirred under reflux under an atmosphere of nitrogen for 3 hours. The mixture was then concentrated in vacuo, acidified with concentrated hydrochloric acid (to pH 2.5), diluted with brine (20 ml) and was extracted three times with ether. The extracts were combined, washed twice with water, dried over anhydrous magnesium sulfate and evaporated to afford 210 mg of the crude product as an oil. This was subject to a column chromatography on silica gel to isolate 200 mg of the homogeneous title D compound as an oil, with consistent spectral data.

D.
[1R[1α,2β(5Z),3β,4α]]-7-[3-[(Hexyloxy)-methyl]-7-oxabicyclo[2.2.1]hept-2-yl]-2,2-dimethyl-5-heptenoyl chloride To a chilled and stirred solution of the title C compound (250 mg, 0.682 mmole) in a mixture of benzene (7 ml) and dimethylformamide (3 drops) was added dropwise oxalyl chloride (0.5 ml, 5.73 mmole) under an atmosphere of nitrogen. After the addition was complete, the solution was stirred at room temperature for 1.5 hours. The solvent was evaporated by a stream of nitrogen and the gummy residue was dried in vacuo at room temperature for one hour to give the crude compound as an oil (262 mg). This was unstable to moisture and was used immediately without characterization.

E.
[1R-[1α,2β(5Z),3β,4α]]-7-[3-[(Hexyloxy)-methyl]-7-oxabicyclo[2.2.1]hept-2-yl]-N-(4-hydroxyphenyl)-2,2-dimethyl-5-heptenamide To a chilled and stirred solution of 4-aminophenol (223 mg, 2.04 mmole), in a mixture of tetrahydrofuran (10 ml) and water (1 ml) was added triethylamine (0.9 ml), followed by a solution of the title E compound (262 mg, 0.681 mmole) in 10 ml of dry tetrahydrofuran. After the addition was complete, the solution was stirred at room temperature under an atmosphere of nitrogen for 1.5 hours. The resulting solution was acidified with 5% hydrochloric acid (to pH 2.5), concentrated in vacuo to remove most of the tetrahydrofuran, saturated with sodium chloride and extracted three times with ethyl ether. The combined ether extracts were dried over anhydrous magnesium sulfate and evaporated in vacuo to give the crude compound as a thick oil. This was chromatographed on silica gel to give 230 mg of the title compound as a thick gummy material, with consistent spectral data.

EXAMPLE 11
[1R-[1α,2β(5Z),3β,4α]]-7-[3-[(Hexyloxy)-methyl]-7-oxabicyclo[2.2.1]hept-2-yl]-N-(4-hydroxy-1-naphthalenyl)-2,2-dimethyl-5-heptenamide To a chilled and stirred solution of 4-amino-1-naphthol hydrochloride (400 mg, 2.04 mmole) in a mixture of tetrahydrofuran (10 ml) and water (1 ml) was added triethylamine (0.9 ml, 6.46 mmole), followed by a solution of the title D compound of Example 10 (260 mg, 0.675 mmole) in 10 ml of dry tetrahydrofuran. After the addition was complete, the solution was stirred at room temperature under an atmosphere of nitrogen for two hours. The resulting solution was acidified with 5% hydrochloric acid (to pH 2.5), concentrated in vacuo to remove most of tetrahydrofuran, saturated with sodium chloride and extracted three times with ethyl ether. The combined ether extracts were washed with water, dried over anhydrous magnesium sulfate and evaporated in vacuo to give a crude compound as a thick oil. This was chromatographed on silica gel to give, after drying in vacuo, 235 mg of the desired compound as a very thick gummy material, with consistent spectral data.

EXAMPLES 12–30

The following additional compounds within the scope of the present invention may be prepared by employing the teachings as outlined above and in the working Examples.

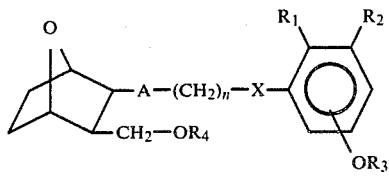

| Ex. No. | R₁ | R₂ | R₃ | R₄ | X | A | n |
| --- | --- | --- | --- | --- | --- | --- | --- |
| 12 | OH | OH | H | $C_5H_{11}$ | O | $CH_2-CH=CH$ | 2 |
| 13 | OH | OH | $C_2H_5$ | $C_5H_{11}$ | $-CH_2-CH_2-NH$ | — | 3 |

-continued

| Ex. No. | R₁ | R₂ | R₃ | R₄ | X | A | n |
|---|---|---|---|---|---|---|---|
| 14 | OH | OH | C₃H₇ | C₃H₇ | $\begin{array}{c}O\\\parallel\\\diagdown C/\\C\\/\ \backslash\\CH_3\ \ CH_3\end{array}$ C—NH— | CH₂—CH=CH | 1 |
| 15 | OH | OH | C₄H₉ | C₄H₉ | —CH₂— | — | 6 |
| 16 | H | O—C₆H₅ | H | C₃H₇ | —NH— | —CH₂—CH=CH— | 3 |
| 17 | cyclohexenyl-O | | H | C₂H₅ | —NH— | —CH₂—CH=CH— | 2 |
| 18 | cyclohexenyl-O | | H | CH₃ | —O— | —CH₂—CH=CH— | 4 |
| 19 | —OCH₃ | —OCH₃ | C₅H₁₁ | CH₂—CH(Cl)—CH₂—CH₃ | —O— | — | 8 |
| 20 | –C₆H₄–O | –C₆H₄–O | H | —CH₂—CH(OH)—CH₃ | —O— | —CH₂—CH=CH— | 4 |
| 21 | —OC₂H₅ | —OC₂H₅ | C₆H₁₃ | C₆H₁₃ | —CH₂—CH₂—CH₂—NH | —CH₂—CH=CH— | 5 |
| 22 | H | H | H | C₆H₁₃ | — | — | 9 |
| 23 | cyclohexenyl-O | | CH₃ | C₇H₁₅ | — | —CH₂—CH=CH— | 3 |
| 24 | cyclohexenyl-O | | H | C₈H₁₇ | NH | —CH₂—CH=CH— | 4 |
| 25 | OH | OH | H | C₆H₁₃ | —CH₂ | (CH₂)₃ | 0 |
| 26 | OH | OH | H | C₆H₁₃ | —NH— | —CH₂—CH=CH— | 4 |
| 27 | OC₄H₉ | OH | H | CH₂—CH=CH—CH₃ | —O— | —CH₂—CH=CH— | 3 |
| 28 | OH | OC₅H₁₁ | H | CH₂—CH₂—CH=CH—CH₃ | —NH— | —CH₂—CH=CH— | 2 |
| 29 | H | H | H | CH₂—C≡C—CH₃ | — | — | 4 |
| 30 | OH | OH | H | CH₂—C≡C—CH₂—CH₃ | —NH— | —CH₂—CH=CH— | 6 |

What is claimed is:

1. A compound of the formula

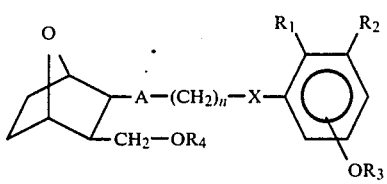

wherein R₁ is hydrogen, hydroxy, alkoxy or aryloxy; R₂ is hydrogen, hydroxy, alkoxy or aryloxy; or wherein R₁ and R₂ taken together is a benzene ring; R₃ is hydrogen or lower alkyl; R₄ is lower alkyl, alkenyl of 2–8 carbon atoms or alkynyl of 2–8 carbon atoms; X is amino, alkylamino, alkanoylamino, oxygen or a single bond; A is —CH₂—CH=Ch— or a single bond; and n is an integer from 0 to 9, with the provisos that when A is a single bond, n is an integer from 1 to 9 and that when X and A are both single bonds, n is an integer from 6 to 9; including all stereoisomers thereof;

wherein the term alkoxy by itself or as part of another group represents both straight and branched chain radicals of up to 12 carbon atoms;

the term alkyl by itself or as part of another group represents both straight and branched chain radicals of up to 12 carbons, chain as well as such groups substituted by F, Br, Cl, I, CF₃, an alkoxy substituent, an aryl substituent, an aralkyl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkythio substituent;

the term aryloxy by itself or as part of another group represents substituted or unsubstituted phenoxy or naphthoxy;

wherein the substituent on either the phenoxy or naphthoxy is selected from the group consisting of 1 or 2 lower alkyl groups, 1 or 2 halogens, 1 or 2 lower alkoxy groups, 1 or 2 hydroxyl groups, 1 or 2 alkylamino groups, 1 or 2 alkanoylamino groups, 1 or 2 nitro groups, 1 or 2 cyano groups, 1 or 2 thiol groups and/or 1 or 2 alkylthio groups.

2. A compound of claim 1 wherein $R_1$, $R_2$ and $R_3$ are each hydrogen, $R_4$ is lower alkyl, A and X are each a single bond and $n=7$.

3. A compound of claim 1 wherein $R_1$ and $R_2$ are each alkoxy, $R_3$ and $R_4$ are alkyl, A is —$CH_2$—CH=CH—, X is oxygen and $n=2$.

4. A compound of claim 1 wherein $R_3$ is hydrogen $R_1$ and $R_2$ are each alkoxy, $R_4$ is alkyl, A is —$CH_2$CH=CH—, X is oxygen and $n=2$.

5. A compound of claim 1 wherein $R_1$ and $R_3$ are hydrogen, $R_2$ is hydroxy, $R_4$ is alkyl, A is a single bond, X is oxygen and $n=7$.

6. A compound of claim 1 wherein $R_1$ is hydrogen, $R_2$ is alkoxy, $R_3$ and $R_4$ are alkyl, A is —$CH_2$—CH=CH—, X is oxygen and $n=4$.

7. A compound of claim 1 wherein $R_1$ and $R_2$ taken together is a benzene ring, $R_3$ is hydrogen, $R_4$ is alkyl, A is —$CH_2$—CH=CH—, X is oxygen and $n=2$.

8. A compound of claim 1 wherein $R_1$ and $R_2$ taken together is a benzene ring, $R_3$ is hydrogen, $R_4$ is alkyl, A is —$CH_2$—CH=CH—, X is oxygen and $n=4$.

9. A compound of claim 1 wherein $R_1$ and $R_2$ are each hydrogen, $R_2$ is hydroxy, $R_4$ is alkyl, A is a single bond, X is oxygen and $n=5$.

10. A compound of claim 1 wherein $R_1$, $R_2$ and $R_3$ are each hydrogen, $R_4$ is alkyl, A is —$CH_2$—CH=CH—, X is amino, and $n=4$.

11. A compound of claim 1 wherein X is

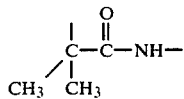

and $n=2$.

12. A compound of claim 11 wherein $R_1$ and $R_2$ taken together is a benzene ring.

13. The compound of claim 1 having the name [1R-[[1α,2β,3β,4α]]-4-[7-[3-[(Hexyloxy)methyl]-7-oxabicyclo[2.2.1]hept-2-yl]heptyl]phenol.

14. The compound of claim 1 having the name [1R-[1α,2β(Z),3β,4α]]-3-[(Hexyloxy)methyl]-2-[5(3,4,5-trimethoxyphenoxy)-2-pentenyl-7-oxabicyclo-[2.2.1]heptane.

15. The compound of claim 1 having the name [1R-[1α,2β(Z),3β,4α]]-5-[5-[3-[(Hexyloxy)methyl]-7--oxabicyclo[2.2.1]hept-2-yl]-3-pentenyl]oxy]-2,3-dimethoxyphenol.

16. The compound of claim 1 having the name [1R-[1α,2β,3β,4α]]-4-[[7-[3-[(Hexyloxy)methyl]-7-oxabicyclo[2.2.1]hept-2-yl]hepty]oxy]-1,2-benzenediol.

17. The compound of claim 1 having the name [1R-[1α,2β(Z),3β,4α]]-3-[(Hexyloxy)methyl]-2-[7-(3,4-dimethoxyphenoxy)-2-heptenyl]-7-oxabicyclo-[2.2.1]heptane.

18. The compound of claim 1 having the name [1R-[1α,2β(Z),3β,4α]]-4-[[5-[3-[(Hexyloxy)methyl]-7-oxabicyclo[2.2.1]hept-2-yl]-3-pentenyl]oxy]-1-naphthalenol.

19. The compound of claim 1 having the name [1R-[1α,2β(5Z),3β,4α]]-4-[[7-[3-[(Hexyloxy)methyl]-7-oxabicyclo[2.2.1]hept-2-yl]-5-heptenyl]oxy]-1-naphthalenol.

20. The compound of claim 1 having the name [1R-[[1α,2β,3β,4α]]-4-[[5-[3-(Hexyloxy)methyl]-7-oxabicyclo[2.2.1]hept-2-yl]pentyl]oxy]-1,2-benzenediol.

21. The compound of claim 1 having the name [1R-[1α,2β(5Z),3β,4α]]-4-[[7-[3-[(Hexyloxy)methyl]-7oxabicyclo[2.2.1]hept-2-yl]-5-heptenyl]amino]phenol monohydrochloride.

22. The compound of claim 1 having the name [1R-[1α,2β(5Z),3β,4α]]-7-[3-[(Hexyloxy)methyl]-7oxabicyclo[2.2.1]hept-2-yl]-N-(4-hydroxyphenyl)-2,2-dimethyl-5-heptenamide.

23. The compound of claim 1 having the name [1R-[1α,2β(5Z),3β,4α]]-7-[3-[(Hexyloxy)methyl]-7oxabicyclo[2.2.1]hept-2-yl]-N-(4-hydroxy-1-naphthalenyl)-2,2-dimethyl-5-heptenamide.

24. A composition for inhibiting allergic conditions in a mammalian species comprising an effective amount of a compound as defined in claim 1 and a pharmaceutically acceptable carrier therefor.

25. A method of simultaneously inhibiting arachidonic acid cyclooxygenase and arachidonic acid 5-lipoxygenase which comprises administering to the circulatory system of a mammalian host an effective amount of a compound as defined in claim 1.

26. The method of claim 25 wherein said compound is administered in an amount within the range of from about 1 to about 100 mg/kg.

27. A method for treating asthma in a mammalian species in need of such treatment, which comprises administering to a mammalian host an effective amount of a compound as defined in claim 28. A method of treating psoriasis in a mammalian species in need of such treatment which comprises administering to a mammalian host an effective amount of a compound as defined in claim 1.

* * * * *

UNITED STATES PATENT AND TRADEMARK OFFICE
CERTIFICATE OF CORRECTION

PATENT NO. : 4,695,585

DATED : September 22, 1987

INVENTOR(S) : Ravi K. Varma et al.

It is certified that error appears in the above-identified patent and that said Letters Patent is hereby corrected as shown below:

Column 17, line 64, "-$CH_2$-CH=Ch' should be -- -$CH_2$-CH=CH- --;

Column 19, line 1, insert --1 or 2 arylcarbonylamino groups, 1 or 2 amino groups-- before "1 or 2 nitro groups";

Column 19, line 1, "1or" should be --1 or--;

Column 19, line 24, "$R_2$" should be --$R_3$--;

Column 19, line 49, --[-- should be inserted before "[5";

Column 20, line 3, "hepty]" should be --heptyl]--;

Column 20, line 46, insert --1.-- after "claim".

Signed and Sealed this

Seventh Day of June, 1988

*Attest:*

DONALD J. QUIGG

*Attesting Officer*     *Commissioner of Patents and Trademarks*